United States Patent [19]

Prozorov et al.

[11] 4,185,633

[45] Jan. 29, 1980

[54] METHOD OF SURGICAL TREATMENT USING LASER EMISSION AND APPARATUS FOR REALIZING SAME

[76] Inventors: Vladimir N. Prozorov, Varshavskoe shosse, 87, kv. 89; Boris N. Malyshev, ulitsa Butlerova, 24, kv. 219; Boris V. Ognev, ulitsa Myaskovskogo, 33/37, kv. 52; Rostislav A. Troitsky, ulitsa Chaikovskogo, 25, korpus 10, kv. 25; Alexandr K. Polonsky, ulista Oxkaya, 16, kv. 124, all of Moscow, U.S.S.R.

[21] Appl. No.: 720,768

[22] Filed: Sep. 7, 1976

[51] Int. Cl.$^2$ ............................................. A61B 17/36
[52] U.S. Cl. .................................. 128/303.1; 128/305
[58] Field of Search ...................... 128/303.1, 305, 395, 128/398, 303.14; 219/121 L, 121 LM

[56] References Cited

U.S. PATENT DOCUMENTS

| | | | |
|---|---|---|---|
| 3,068,739 | 12/1962 | Hicks, Jr. et al. ............... | 128/395 X |
| 3,467,098 | 9/1969 | Ayres ............................... | 128/395 X |
| 3,538,919 | 11/1970 | Meyer .............................. | 128/398 |
| 3,693,623 | 9/1972 | Harte et al. ..................... | 128/303.1 |
| 3,821,510 | 6/1974 | Muncheryan .................. | 128/303.1 X |
| 3,826,263 | 7/1974 | Cage et al. ...................... | 128/303.1 |
| 4,074,718 | 2/1978 | Morrison, Jr. .................. | 128/303.14 |
| 4,126,136 | 11/1978 | Auth et al. ...................... | 128/303.1 |

*Primary Examiner*—Lee S. Cohen
*Attorney, Agent, or Firm*—Steinberg & Blake

[57] ABSTRACT

Biological tissue is dissected by means of a mechanical cutting instrument, while the coagulation of the walls of the incision is effected simultaneously with the dissection by means of a laser beam, for which a laser beam spot is formed in the immediate proximity to the cutting instrument's cutting edge. An apparatus for the realization of this method combines a mechanical cutting instrument made preferably of a material transparent to laser emission, and a structure for the formation of a laser beam spot in the immediate proximity to the cutting instrument's cutting edge. In the preferred embodiment the cutting instrument itself provides for the formation of the spot close to the cutting edge.

6 Claims, 2 Drawing Figures

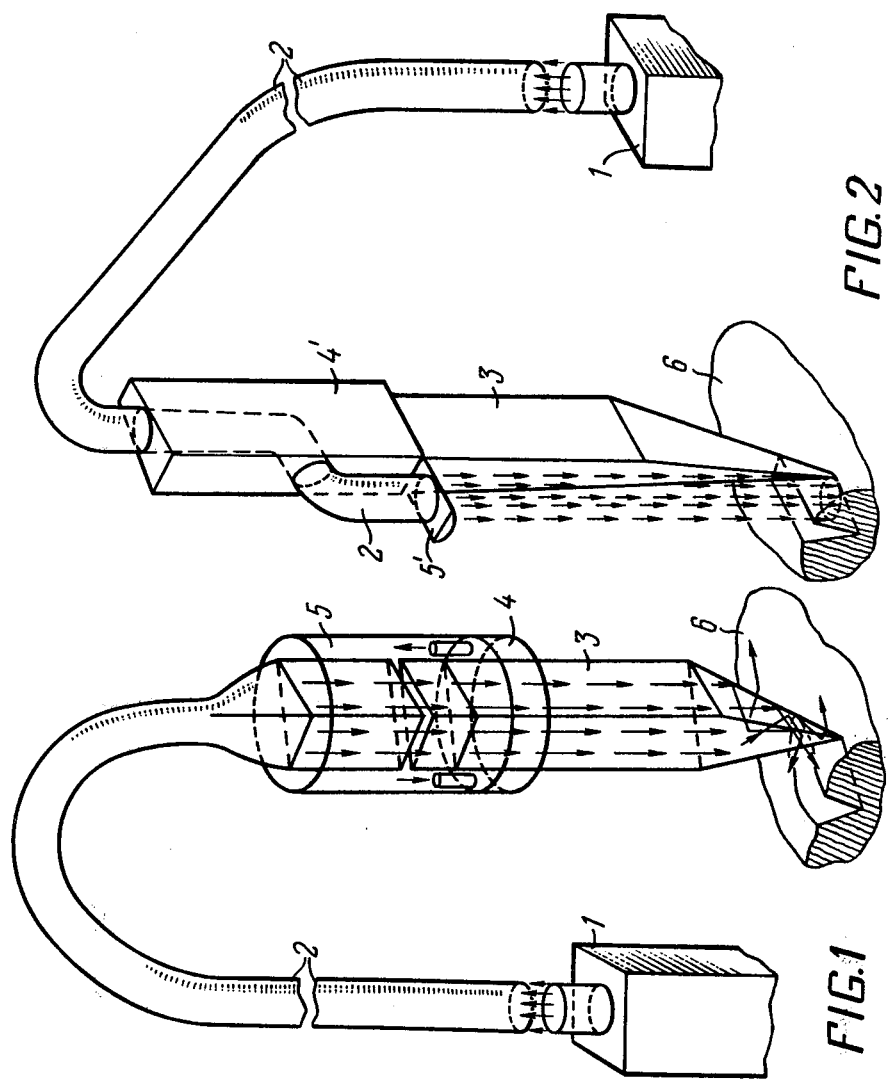

METHOD OF SURGICAL TREATMENT USING LASER EMISSION AND APPARATUS FOR REALIZING SAME

BACKGROUND OF THE INVENTION

This invention relates to medicine and more particularly, to a method of surgical treatment using a laser beam and an apparatus for realizing said method. This invention may be used with the greatest advantage for dissection of the skin, muscles, the liver, the spleen, intestinal walls, the stomach, kidneys, the uterus, the ovaries, lymph nodes, and in any other cases calling for the minimum bleeding during dissection.

As is known, the use of a laser beam in surgery is becoming more and more widespread of late. Usually, a laser pencil beam with an energy density of $10^4$–$10^5$ Wt/cm$^2$ is directed at the area being dissected. The tissues dissected in this way are then joined together, for example, with a silk suture.

This method of surgery, however progressive, still has a number of disadvantages, one of them, and the main one, being that, with the aforementioned energy densities it is not ruled out that along with the dissection of the necessary parts of biological tissue additional areas of tissue which should not be dissected may in fact be dissected. This is particularly dangerous in cases when the operation involves tissues surrounding major blood vessels.

Attention should also be drawn to the fact that part of the dissected walls get charred due to the great amount of energy released, which adversely affects the conditions for the subsequent union of biological tissue.

It is an object of the invention to provide a method of surgical treatment that, while allowing to control the depth of the incision, would reduce loss of blood during dissection.

Another object of the present invention is to provide conditions conducive to the good union of biological tissues.

Still another object of the invention is to provide a device for surgical treatment allowing to control the depth of the incision and reduce the loss of blood.

BRIEF DESCRIPTION OF THE INVENTION

These and other objects are attained in that in surgical treatment biological tissue is dissected with the aid of a mechanical cutting instrument, while photocoagulation of the dissected walls is effected with a laser beam.

The density of the laser beam is $10^2$–$10^3$ Wt/cm$^2$.

The advantage of this invention is that the mechanical cutting instrument permits to conduct dissection to a strictly controlled depth, while the laser beam provides for the simultaneous mild coagulation of the dissected walls without charring them, which results in a minimum loss of blood.

A photocoagulating laser beam spot may be formed in the immediate proximity to the cutting instrument's cutting part, behind it in the direction of its movement during dissection. However, it is most expedient to effect the emergence of the laser beam through the cutting part of the mechanical cutting instrument.

The proposed method can be realised by means of a concurrently disclosed device comprising a mechanical cutting instrument made of a material transparent for laser emission, possessing the maximum refraction coefficient for the given wavelength of the laser emission, as a result of which the cutting instrument itself serves as the means for forming the laser beam spot.

Sapphire or germanium may be used as the material for the cutting instrument.

BRIEF DESCRIPTION OF THE DRAWINGS

The invention will now be described with reference to preferred embodiments of the device for surgical treatment, in accordance with the invention, taken in conjunction with the accompanying drawings, wherein:

FIG. 1 is a schematic view of the apparatus for surgical treatment, in accordance with the invention, with the laser beam emerging right through the cutting part of the mechanical cutting instrument;

FIG. 2 shows another apparatus for realizing the disclosed method, but providing for the formation of the laser spot in the immediate proximity to and behind the cutting part.

DETAILED DESCRIPTION OF THE INVENTION

With reference to FIG. 1, the apparatus for surgical treatment, in accordance with the invention, comprises a laser 1, a movable laser light guide 2, a mechanical cutting instrument 3, a cooling jacket 4 (gaseous or liquid) of the cutting instrument, and a grip 5. Designated under number 6 is the biological tissue being dissected.

Any laser that provides an energy density of the order of $10^2$–$10^3$ Wt/cm$^2$, sufficient for performing the surgical operation, can be used as the laser 1.

Used in our investigations were argon, carbon dioxide and garnet (with neodymium) lasers. However, the use of other lasers is also possible, their choice appearing obvious to any specialist versed in the art.

The light guide 2 is made mobile in the form of a flexible fiberglass braid or a hinged mirror system in order to enable the surgeon to move the terminal outlet part of the light guide within six degrees of freedom.

The mechanical cutting instrument 3 is essentially a cylindrical body with a pointed end portion, forming the cutting part of said instrument. In the general case the cutting part is made similar to a conventional metal surgical scalpel. The instrument is made of a hard material, transparent to laser emission, e.g. sapphire or germanium.

The cutting instrument has a constant section near the entry butt end and in the middle part which smoothly tapers off in the direction of the pointed cutting part. Their surfaces are flat and are treated as polished optical surfaces. The butt portion of the instrument is also flat and is likewise treated as a polished optical surface. Adjoining it is the light guide with a cross-section equal to the cross-sectional area of the butt end of the cutting instrument.

The laser beam passes through the light guide and enters the cutting instrument. In the butt end and middle portions of the cutting instrument the beam spreads without emerging beyond its boundaries and without any alteration of cross-sectional radiation density or any changes in angles of incidence (greater than the critical angle). In the pointed cutting part of the instrument the cross-sectional beam density increases as the angles of incidence onto the inner surfaces of the instrument diminish down to angles less than the critical near its edge.

During the operation the cutting instrument is cooled with a liquid (water, liquid nitrogen, etc.) or gaseous (air, gaseous nitrogen, etc.) coolant.

Referring now to FIG. 2, another embodiment of the apparatus for surgical treatment, in accordance with the invention, comprises a laser 1, a movable laser light guide 2 and, in addition, a metal cutting instrument 3, an optical element 5', partially focusing the laser beam, and grip 4'. Designated under the number 6 is the biological tissue being dissected.

The light guide and the optical element are fastened to the grip so as to direct the laser beam to the rear portion (opposite the cutting edge) of the cutting instrument.

Handling of the apparatus is the same in both cases. The surgeon switches on the laser, takes hold of the cutting instrument's grip and performs the dissection of the biological tissue with the instrument's cutting edge to the required depth. All the while photocoagulation and hemostasis of the dissected walls take place actually simultaneously with the formation of the incision.

The use of the proposed invention makes it possible to considerably reduce loss of blood during surgery.

Thus it will be seen that with the method and apparatus of the invention, biological tissue is dissected by the cutting edge of a mechanical cutting means while a laser beam is directed from a location spaced from this cutting edge to the dissected tissue substantially simultaneously with the cutting thereof for effecting the photocoagulation of the dissected tissue.

What is claimed is:

1. A surgical treatment method comprising dissecting biological tissue with a cutting edge of a mechanical cutting means and directing a laser beam from a location spaced from said cutting edge to form therefrom a spot situated in the immediate proximity of the cutting edge just behind said mechanical cutting means in the direction of movement thereof during dissection substantially simultaneously with the dissection of the tissue for effecting photocoagulation of the dissected tissue.

2. Surgical treatment apparatus comprising mechanical cutting means having a cutting edge for dissecting biological tissue, and means operatively connected with said mechanical cutting means for directing a laser light beam from a location spaced from said cutting edge to the region of said cutting edge at a location situated immediately behind the same for effecting coagulation of tissue cut by said cutting edge.

3. Surgical treatment apparatus comprising mechanical cutting means which is transparent to laser emission, said cutting means having a cutting edge for dissecting biological tissue; means operatively connected with said mechanical cutting means for directing a laser light beam from a location spaced from said cutting edge to the region of said cutting edge for effecting coagulation of tissue cut by said cutting edge; and cooling jacket means operatively connected with said mechanical cutting means for cooling the same.

4. The combination of claim 3 and wherein said mechanical cutting means has a configuration for concentrating said beam in the form of a spot at the region of said cutting edge.

5. The combination of claim 3 and wherein said mechanical cutting means is made of sapphire.

6. The combination of claim 3 and wherein said mechanical cutting means is made of germanium.

* * * * *